US00PP12576P2

(12) United States Plant Patent
Yates

(10) Patent No.: US PP12,576 P2
(45) Date of Patent: Apr. 23, 2002

(54) JAMESBRITTENIA PLANT NAMED 'YAGEPIN'

(76) Inventor: Frederic Yates, Poplar Nursery, Holmes Chapel Rd., Somerford, Congleton, Cheshire (GB), CW12 4FP ( * ) Notice: Subject to any disclaimer, the term of this patent is extended or adjusted under 35 U.S.C. 154(b) by 0 days.

(21) Appl. No.: 09/689,327

(22) Filed: Oct. 12, 2000

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Mark P. Bourgeois

(57) ABSTRACT

A new and distinct cultivar of Jamesbrittenia plant named 'Yagepin', characterized by unique small marginally lobed leaves and pink-colored flowers, making it a new hanging basket distinct from all other varieties known to the inventor.

2 Drawing Sheets

CROSS-REFERENCES TO RELATED APPLICATIONS

This application corresponds to two other applications entitled Jamesbrittenia Plant Named 'Yagero' (U.S. patent application Ser. No. 09/689,332) and Jamesbrittenia Plant Named 'Yagevi' (U.S. patent application Ser. No. 09/689,324), both of which have the same inventor and filing date as the present invention.

BACKGROUND OF THE INVENTION

The present invention relates to a new and distinct cultivar known botanically as a Jamesbrittenia of hybrid origin and referred to hereinafter by the cultivar name 'Yagepin'. The genus Jamesbrittenia has been split from the genus Sutera under which plants of Jamesbrittenia have hitherto been classified.

The new cultivar was bred and selected from a long term breeding program aimed at producing new forms and colors of patio plants and hanging baskets. The exact parents of 'Yagepin' are unidentified Jamesbrittenia species hybrids. The original breeding material included Jamesbrittenia species *jurassica, breviflora, microphylla* and *pristisepala* (none of these have been patented). Through open pollination the species hybridized producing many generations of seedlings. From these seedlings that resulted from various unidentified crosses of Jamesbrittenia species, four new selections were made. The breeding program was conducted by the inventor in a cultivated area of Congleton, Chesire England. The inventor conducted the first crosses in the summer of 1992 and made four selections in 1999, of which 'Yagepin' was one. The method of origination or breeding technique was seedling selection and re-selection, followed by asexual propagation using cuttings.

'Yagepin' was selected for its characteristics as a new patio plant and hanging basket and can be distinguished as unique by its leaf size, leaf shape and flower color. The foliage of 'Yagepin' resembles the co-pending applicants 'Yagero' and 'Yagevi', however, it is unique from others existing in the trade due to its smaller and marginally lobed leaves. In flower color 'Yagepin' differs from the co-pending varieties by exhibiting pink flowers. In comparison, 'Yagero' flowers are rose-colored and 'Yagevi' flowers are violet-colored.

The first asexual propagation was conducted by the inventor in Congleton, Chesire England in 1999, using cuttings. The new cultivar has been found stable through many cycles of vegetative propagation and remains true to type demonstrating no off-types in successive generations.

SUMMARY OF THE INVENTION

The following traits have been repeatedly observed and represent the characteristics of the new cultivar. These attributes in combination distinguish this cultivar from all other varieties known to the inventor. 'Yagepin' is a new selection for a basket due to its leaf size and shape, and its flower color. The foliage is similar to 'Yagero' and 'Yagevi', however, the leaves are smaller and marginally lobed as compared to all other existing varieties in the trade. Pink-colored flowers distinguish 'Yagepin' from the two co-pending varieties; 'Yagero' which exhibits rose-colored flowers, and 'Yagevi' which exhibits violet-colored flowers.

BRIEF DESCRIPTION OF THE DRAWINGS

The accompanying color photographs illustrate the overall appearance of the new cultivar.

The photo on sheet 1 is a good representation of the plant showing flower color, foliage, and habit of the plant.

The photo on sheet 2 gives a close-up view of stems with the 'Yagepin' flowers on the left and the 'Yagevi' flowers on the right. All photographs are taken of plants grown in one-gallon containers. The prints are made using conventional photographic techniques and although colors may appear different from actual colors due to light reflectance they are as accurate as possible by conventional photography.

BOTANICAL DESCRIPTION OF THE PLANT

The following is a detailed description of the new cultivar as grown in a one-gallon container under greenhouse conditions in Encinitas Calif. Phenotypic differences may be observed with variations in environmental, climatic and cultural conditions. The color determinations are in accordance with The Royal Horticultural Society Colour Chart except where general color terms of ordinary dictionary significance are used.

Botanical classification: Jamesbrittenia 'Yagepin'.

Common name: Bacopa.
Use: Hanging basket, patio plant.
Parentage: The parents of 'Yagepin' are Jamesbrittenia species hybrids.
*Seed parent.*—Unidentified Jamesbrittenia species hybrid.
*Pollen parent.*—Unidentified Jamesbrittenia species hybrid.
Propagation: Vegetative cuttings.
Type: Annual.
Root system: Fibrous.
Special growing requirements: Shear after heavy flowering.
Seasonal interest: Profuse and colorful floral display.
Cropping time: 8 weeks to root from cutting.
Diseases and pests: Potential for mildew.
Growth habit: Upright and cascading.
Height: 45 cm. high.
Width: 45 cm. wide.
Hardiness: Observed as hardy from −5 to 15 degrees Centigrade, however hardiness has not been fully tested.
Soil: Free-draining.
Light levels: Plant in part shade to full sun.
Stem shape: Cylindrical.
Stem color: 144A.
Stem size: 28 cm. long by 2 mm. wide.
Internode length: 1–2 cm. between nodes.
Stem surface: Slightly sticky, stipitate glandular.
Foliage:
*Leaf arrangement.*—Alternate.
*Leaf division.*—Simple.
*Shape.*—Lyrate but with lobes continuing toward apex.
*Base.*—Cuneate.
*Apex.*—Retuse with two shallow notches.
*Venation.*—Prominent mid-vein with veins diverging to lobes.
*Margins.*—Cleft with stipitate glandular edges.
*Surface.*—Viscid and stipitate glandular.
*Length.*—6 mm. long.
*Width.*—4 mm. wide.
*Color* (*upper surface*).—139B.
*Color* (*lower surface*).—138A.
*Petiole.*—3 mm. long and 1 mm. wide.
*Foliar fragrance.*—Mild turpentine-like scent.

Flower:
*Type.*—Solitary.
*Shape.*—Circular, rotate.
*Margins.*—Entire.
*Surface.*—Glabrous.
*Fragrance.*—None observed.
*Flower size.*—1.5 cm. wide by 1 cm. high.
*Flowering season.*—Spring and summer.
*Flowering time.*—Diurnal.
*Aspect.*—Facing outward and upward.
*Peduncle length.*—1.5–2 cm. long.
*Peduncle width.*—1 mm. wide.
*Peduncle color.*—139C.
*Persistent or non-persistent.*—Persistent.
*Petals.*—Five petals.
*Fused or unfused.*—Fused.
*Petal color.*—84B with dark rim 59A at edge of throat.
*Throat markings.*—Sunburst 17A with edges 155D.
*Calyx surface.*—Stipitate glandular.
*Calyx size.*—2 mm. wide by 3 mm. high.
*Calyx color.*—139B,C.
*Sepal color.*—139A,B.
*Sepal width and length.*—1 mm. wide by 3 mm. high.
*Sepal number.*—Five.
Reproductive organs:
*Stamens.*—Two stamens.
*Stamen dimensions.*—6–7 mm. in length and 0.50 mm. in diameter.
*Pollen color.*—15A.
*Pistil color.*—144C.
*Number of pistils.*—One in number.
*Pistil dimensions.*—6.5–7.5 mm. in length and 0.75 mm. in diameter.
Seed production:
*Seed shape.*—Spherical in shape.
*Seed dimensions.*—0.60–0.75 mm. in diameter and 0.60–0.75 mm. in height.
*Seed color.*—199B.
*Capsule color.*—200A.
*Capsule dimensions.*—2.5 mm. in diameter and 6 mm. in length.
*Capsule shape.*—Ovate.
*Seed surface.*—Glabrous.
*Seed quantity.*—30–40 per capsule.

I claim:

1. A new and distinct cultivar of Jamesbrittenia plant named 'Yagepin' as described and illustrated.

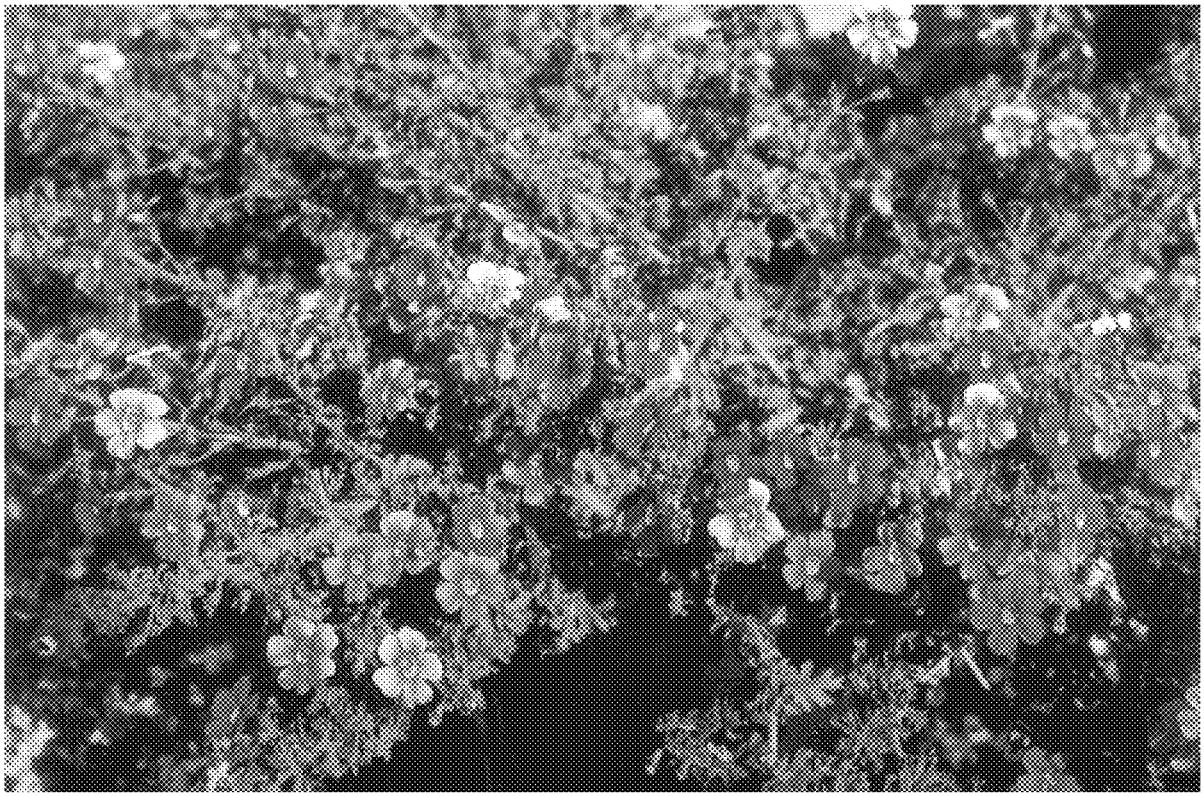

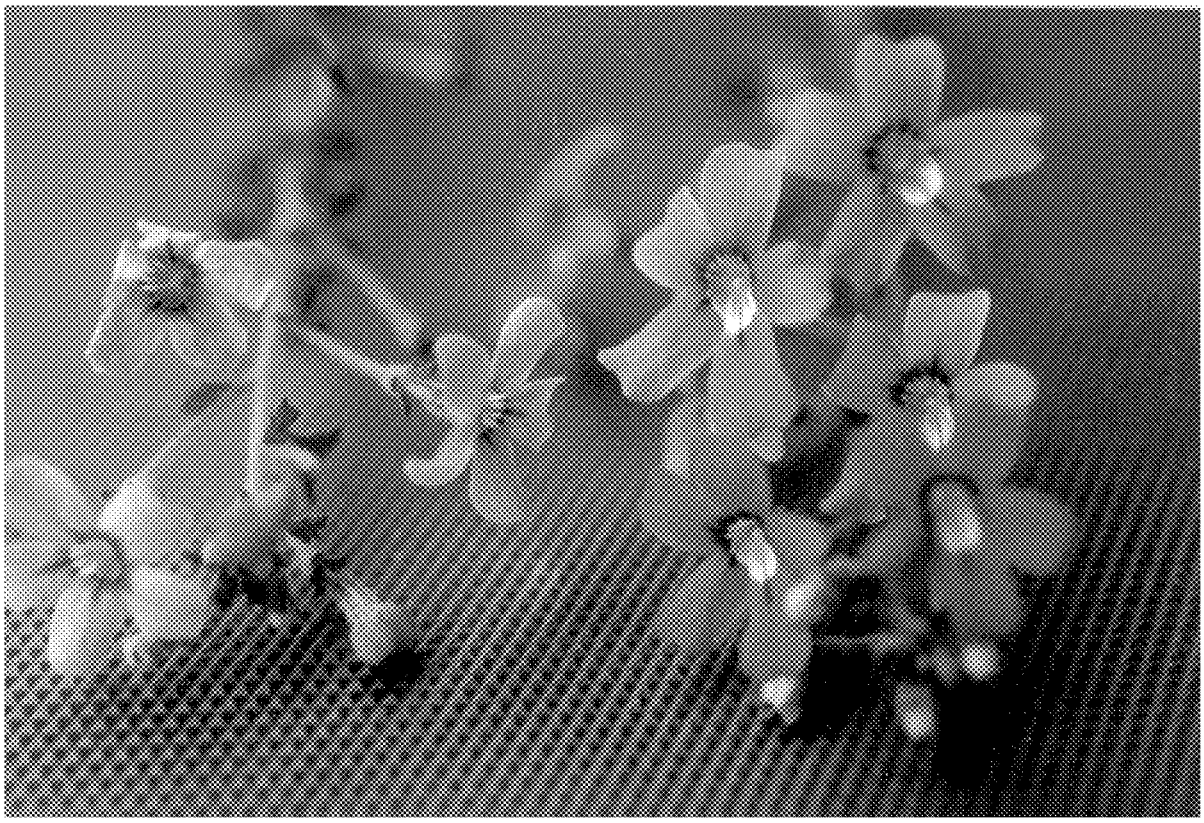

* * * * *